United States Patent [19]

Haacke et al.

[11] Patent Number: 4,724,386

[45] Date of Patent: Feb. 9, 1988

[54] CENTRALLY ORDERED PHASE ENCODING

[75] Inventors: E. Mark Haacke, University Heights; Carolyn A. Kershaw, Mentor; John L. Patrick, Solon, all of Ohio

[73] Assignee: Picker International, Inc., Highland Hts., Ohio

[21] Appl. No.: 798,551

[22] Filed: Nov. 15, 1985

Related U.S. Application Data

[63] Continuation-in-part of Ser. No. 782,075, Sep. 30, 1985, which is a continuation-in-part of Ser. No. 764,439, Aug. 9, 1985, which is a continuation-in-part of Ser. No. 731,509, May 7, 1985, Pat. No. 4,678,996.

[51] Int. Cl.$^4$ ............................................. G01R 33/20
[52] U.S. Cl. .................................... 324/309; 128/653; 128/721; 324/312; 324/314
[58] Field of Search ............... 324/309, 306, 313, 314, 324/312; 128/653, 721-723

[56] References Cited

U.S. PATENT DOCUMENTS

| | | | |
|---|---|---|---|
| 4,303,077 | 12/1981 | Lewin et al. | 128/777 |
| 4,454,384 | 10/1985 | Kawachi | 128/653 |
| 4,516,075 | 5/1985 | Moran | 324/309 |
| 4,564,017 | 1/1986 | Glover | 128/653 |
| 4,567,893 | 2/1986 | Charles et al. | 128/653 |
| 4,574,240 | 3/1986 | Libove et al. | 324/306 |
| 4,581,582 | 4/1986 | Redington | 324/309 |
| 4,591,789 | 5/1986 | Glover et al. | 324/307 |
| 4,614,195 | 9/1986 | Bottomley et al. | 128/653 |
| 4,616,180 | 10/1986 | Compton | 324/309 |
| 4,616,183 | 10/1986 | Glover et al. | 324/309 |
| 4,618,827 | 10/1986 | Redington | 324/309 |
| 4,678,996 | 6/1987 | Haack et al. | 324/309 |

FOREIGN PATENT DOCUMENTS

| | | |
|---|---|---|
| 0096487 | 12/1983 | European Pat. Off. |
| 0117725 | 9/1984 | European Pat. Off. |
| 0130479 | 1/1985 | European Pat. Off. |
| 0167350 | 1/1986 | European Pat. Off. |
| 0172345 | 2/1986 | European Pat. Off. |
| 2854774 | 7/1980 | Fed. Rep. of Germany |
| 2027208 | 2/1980 | United Kingdom |

OTHER PUBLICATIONS

"Magnetic Resonance Imaging with Respiratory Gating: Techniques and Advantages" by Ehman, et al., AJR 143, Dec. 1984, pp. 1175–1182.

"Cardiac Response to Pulsed Magnetic Fields with Regard to Safety in NMR Imaging" by McRobbie, et al., 2362 Physics in Medicine & Biology 30 (1985) Jul., No. 7, pp. 695–702.

"Respiratory Gating in Magnetic Resonance Imaging at 0.5 Tesla", V. M. Runge et al., Radiology, vol. 151, No. 2, pp. 521–523 (1984).

"MR Image Artifacts from Periodic Motion" by Michael Wood and Mark Henkelman, Med. Phys. 12(2), Mar./Apr. 1985, pp. 143–151.

International Search Report dated Nov. 25, 1986.

*Primary Examiner*—Tom Noland
*Attorney, Agent, or Firm*—Fay, Sharpe, Beall, Fagan, Minnich & McKee

[57] ABSTRACT

A portion of a subject (22) which is undergoing respiratory or other motion is disposed in an image region (20) to be examined. A respiratory or other motion monitor (50) monitors the cyclic respiratory motion and provides output signals indicative of chest expansion. A phase encoding gradient selector (60) selects the phase encoding gradient that is to be applied by a gradient magnetic field controller (40) and coil (42). A central phase encoding gradient is selected corresponding to a chest relaxation extreme and minimum and maximum phase encoding gradients are selected corresponding to a chest expansion extreme (FIG. 2). Intermediate degrees of monitored physical movement cause the selection of corresponding intermediate phase encoding gradients. Resonance signals collected during each phase encoding gradient are Fourier or otherwise transformed (80) into a corresponding view. A filter (92) weights each view such that views closest to the central phase encoding gradient are weighted most heavily and views adjacent the minimum and maximum phase encoding gradients are weighted least heavily. The physical position of pixels within each view are scaled (94) to adjust each view in accordance with the degree of physical expansion. The weighted and scaled views are transformed into an image memory (120) for display on a video display (122) or the like.

25 Claims, 7 Drawing Figures

FIG. I

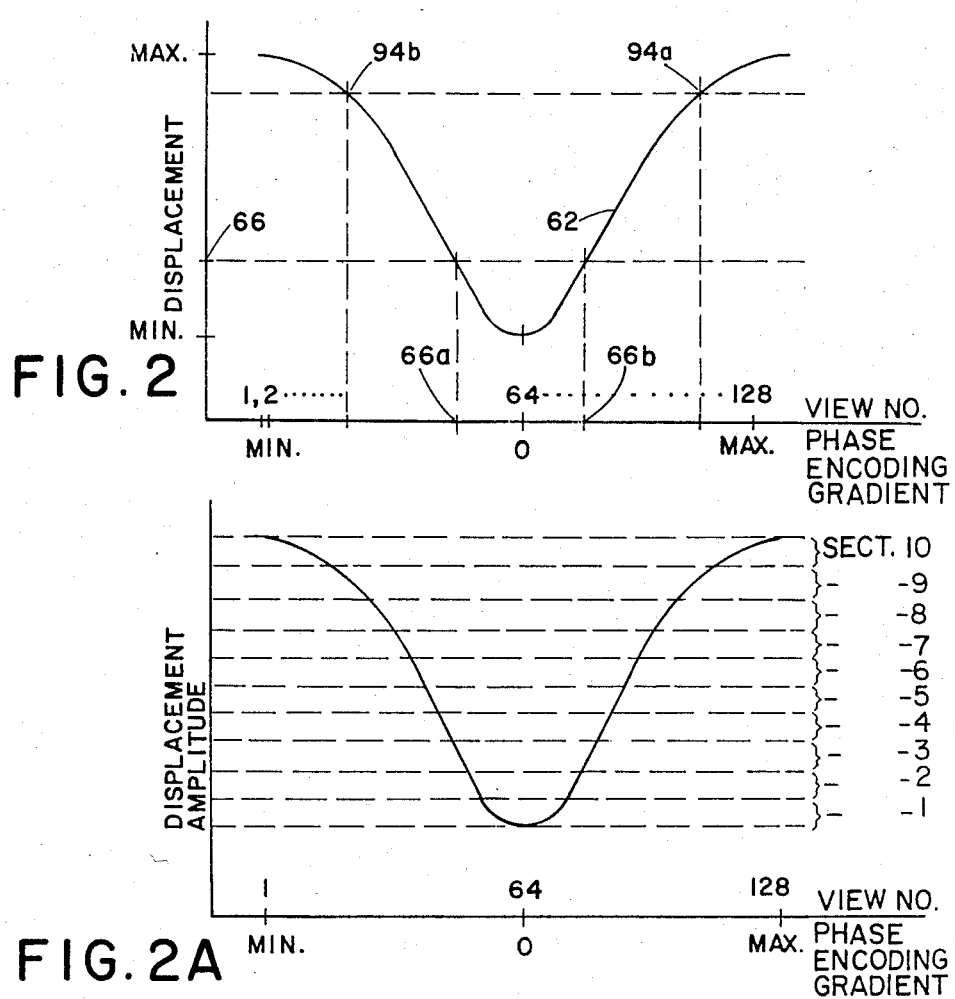
FIG. 2
FIG. 2A
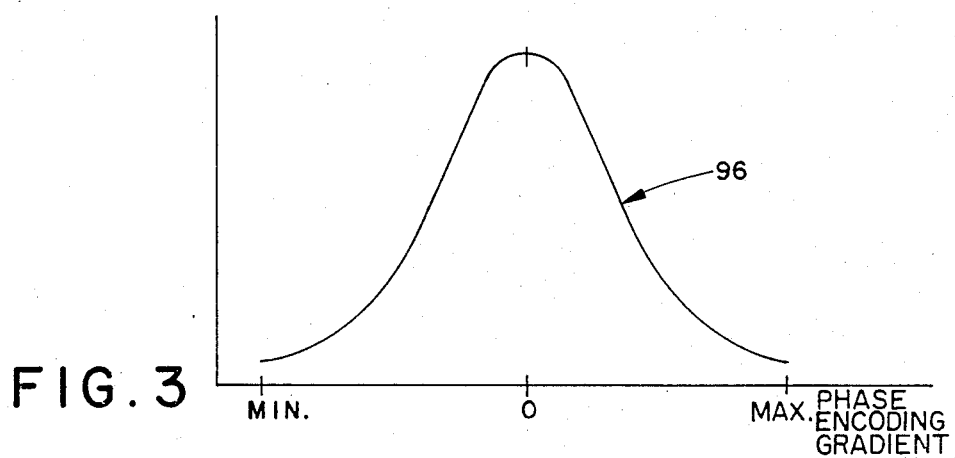
FIG. 3

CENTRALLY ORDERED PHASE ENCODING

This application is a continuation-in-part of application Ser. No. 782,075 filed Sept. 30, 1985, which is a continuation-in-part of application Ser. No. 764,439 filed Aug. 9, 1985, which in turn is a continuation-in-part of application Ser. No. 731,509 filed May 7, 1985 now U.S. Pat. No. 4,678,996.

BACKGROUND OF THE INVENTION

The present invention relates to the art of nuclear magnetic resonance. Particular application is found in conjunction with magnetic resonance imaging in regions of a patient undergoing periodic respiratory movement and description will be made with reference thereto. It is to be appreciated, however, that the present invention is also applicable to monitoring other objects which have moving portions, such as imaging regions of a patient adjacent the heart, regions with periodic cardiovascular expansion and contraction, regions with spasmodic muscular action, and other regions of animate and inanimate objects with moving portions or components.

Heretofore, magnetic resonance imaging included positioning the patient in a strong substantially uniform, longitudinal magnetic field. Magnetic dipoles were caused to precess, generating magnetic resonance signals. Various known techniques have been utilized to select a region of the patient to be imaged and are well known in the art. Magnetic field gradients were applied orthogonally to encode spatial position into a selected slice or planar region of interest. The magnetic field gradients were encoded along one axis giving a frequency which varied linearly in accordance with position and along an orthogonal axis giving a phase that varied linearly in accordance with position.

The resonance signal was collected with each of a plurality of phase encodings and transformed from a frequency and phase domain to an image or spatial domain. In the image domain, each transformed resonance signal produced a view representing the density of resonating nuclei in each pixel or incremental area of the image region. The amplitude of the phase encoding gradient was incrementally increased with equal steps from view to view to collect a plurality of views, commonly on the order of 128 views. The plurality of views were transformed to create an image representing the density of resonating nuclei in each pixel or incremental area of the image region.

When a portion of the patient or object in the image region was moving, the movement tended to cause a blurring in the resultant image. However, in conventional Fourier transform reconstruction imaging, the blur was not limited to the moving portions. Rather, the distortion was spread across the entire picture in the phase encoding direction. This blurring was commonly manifested in the resultant image as "ghost" artifacts or multiple superimposed coherent image replications along the phase encoding direction or as distributed noise. Moreover, there was an effective periodicity between the respiratory movement and phase encoding gradient over the full image collection cycle. The periodicity enhanced multiple superimposed coherent ghosting.

One solution to respiratory motion artifacts was to gate view collection in accordance with the respiratory cycle. That is, data were only generated when the respiratory movement was at some fixed value, usually near its minimum. A first plurality of views were taken starting with the minimum, negative phase encoding gradient and incrementing upward during a first period of minimum respiratory movement. When the respiratory motion increased beyond a preselected value, the phase encoding and data collection were terminated until the next respiratory cycle. Successive pluralities of phase encoded views were taken in each subsequence minimum movement period. This process was continued until data were collected with a maximum, positive phase encoding gradient, commonly 128 views later. Disruption in data collection during periods of greater respiratory movement or a change in the pattern of respiration increased the duration required to generate an image.

A second solution was to reorder the data to reduce the periodicity of the motion. The loss of image resolution and ghosting attributable to respiratory movement has been reduced by negating the effective periodicity of the respiratory motion. Specifically, the phase encoding gradient values were re-ordered such that at the minimum motion portion of the respiratory cycle, the collected view was phase encoded with the minimum or negative most phase encoding gradient; during the maximum respiratory movement, the collected view was phase encoded with a maximum or positive most phase encoding gradient. Commonly, the minimum phase encoding gradient and the maximum phase encoding gradient were encoded at generally the same spatial frequency but with one delayed and the other advanced such that the minimum phase encoding gradient was negative and the maximum phase encoding gradient was positive. Between the minimum and maximum points of motion the phase was encoded in a linearly proportional relationship between phase encoding gradient and rate or degree of respiratory motion. The median degree of motion midway between the extremes was encoded with a central phase encoding, commonly at the lowest spatial frequency. In this manner, the motion-induced artifacts were reduced by converting the periodicity effectively into a single respiratory period.

One of the drawbacks of this re-ordering scheme was that the data collected during the greatest and the least rates of motion were both encoded at the highest spatial frequencies. Collecting the views with intermediate amounts of motion around the central or zero phase encoding caused a lack of symmetry in the collected data. Certain spatial frequency components were selected preferentially as being less affected by motion in an asymmetric fashion. That is, negative high spatial frequencies were less affected while positive high spatial frequencies were more affected. This had an adverse effect on the point spread function and resolution of the resultant image. It was also a probelm when a smoothing filter was applied because this filter rejected the negative highest spatial frequencies which contain the region of minimal motion (i.e. some of the best data is rejected).

Yet another difficulty resided in the one to one mapping by a probability distribution. Also, in certain patterns of breathing which had essentially no periods of rest, this data was not used most effectively. Further, the technique tended to misplace views near the center (i.e., violated the monotonically increasing function aspect) and hence the method was not robust. Because significant motion may have occurred in the region of low spatial frequency where the signal power was the greatest, the image could still have significant motion artifacts.

Memory limitations restrict the taking of multiple average and multiple slice data.

A further disadvantage of the prior art was that any mapping or reordering of the phase encoding with the amplitude of the motion could not correct the motion. Because motion was not eliminated, an inherent loss of resolution resulted.

The present invention contemplates a new and improved centrally ordered or symmetric phase encoding technique which overcomes the above referenced problems and others.

SUMMARY OF THE INVENTION

In accordance with one aspect of the present invention, an improved method of magnetic resonance imaging is provided. A subject with a moving portion is positioned in an image region. Magnetic dipoles are excited to resonance in at least a portion of the subject in the image region. The subject's movement is monitored and a phase encoding gradient is selected in accordance therewith. Each phase encoding gradient is selected from a set of phase gradients that range to either side of a central phase gradient (e.g. zero) between a maximum and a minimum. The selection is made such that during periods of least physical movement, the phase encoding gradient is selected closest to one of (i) the central phase gradient and (ii) distributed between the minimum and maximum and during periods of greatest physical movement, the phase encoding gradient is selected the closest to the other. Magnetic field gradients with the selected phase encoding gradient spatially encode the resonating magnetic dipoles. Resonance signals are received from the resonating dipoles and are reconstructed into an image representation.

In accordance with a more limited aspect of the present invention, the received resonance signals are filtered symmetrically to delete or de-emphasize signals with the phase encoding selected during the periods of greatest motion.

In accordance with another more limited aspect of the invention, each collected view is scaled in accordance with the selected phase encoding gradient with which the view was generated, hence, with the degree of physical movement of the subject portion.

In accordance with another aspect of the present invention, a magnetic resonance imaging apparatus is provided. A main magnetic field means creates a main magnetic field in the image region. A magnetic resonance excitation means excites resonance of magnetic dipoles in the image region. A gradient field means selectively causes magnetic field gradients across the main magnetic field at least in the image region for at least phase encoding the resonance signals from the resonating magnetic dipoles in accordance with spatial position within the image region. A monitoring means monitors physical movement of at least a portion of the subject in the image region. A phase encoding gradient selection means selects a phase encoding gradient from a preselected set of gradients in accordance with the monitored physical movement and causes the gradient means to encode phases with the selected phase encoding gradient. The phase encoding gradient selection means selects the phase encoding gradient such that either the greatest monitored physical movement or the least monitored physical movement is phase encoded with a central phase encoding gradient and the other is encoded with minimum and maximum phase encoding gradients. Intermediate amounts of motion are phase encoded with intermediate encoding gradients between the central phase encoding gradient and the minimum or maximum phase encoding gradient. A reconstruction means reconstructs a view from the resonance signal with each phase encoding for transformation into an image representation.

In accordance with other aspects of the present invention, a filter means filters the resonance data or views to emphasize the views which are phase encoded with phase encoding gradients corresponding to the least physical movement and de-emphasize or eliminate views phase encoded with phase encoding gradients corresponding to maximum physical movement. The region of least physical movement can be chosen to correspond with any desired spatial frequency.

In accordance with another aspect of the invention, a scaling means is provided for scaling the moving portion of the subject in each view in accordance with the positional change and hence the phase encoding gradient to compensate for the effects of the motion. In this manner, loss of resolution due to the motion is corrected.

One advantage of the present invention is that the spatial frequencies are affected symmetrically. This optimizes amplitude and phase response in the image and enables the use of resolution improving filters. It also makes the technique robust in that it includes the highest signal power with the least motion.

Another advantage is that the present invention facilitates sectioning to allow for more flexibility in selecting coverage of the respiratory pattern and makes the technique more robust for respiratory pattern changes. It also facilitates multiple average and multiple slice acquisition.

Yet another advantage of the present invention is that two orders of motion correction are provided. Central ordering of the phase encoding corrects for motion induced ghosting and artifacts and scaling or other modeling techniques correct for loss of resolution attributable to the motion itself.

Still further advantages of the present invention will become apparent to those of ordinary skill in the art upon reading and understanding the following detailed description of the preferred embodiments.

BRIEF DESCRIPTION OF THE DRAWINGS

The invention may be embodied in various parts and arrangements of parts or in various steps and arrangements of steps. The drawings are only for purposes of illustrating the preferred embodiment and are not to be construed as limiting the invention.

FIGS. 2 and 2A are graphic representations of a preferred centrally ordered phase encoding scheme in accordance with the present invention;

FIG. 3 is a graphic illustration of an exemplary filter function for use in conjunction with the phase encoding scheme of FIG. 2;

DETAILED DESCRIPTION OF THE PREFERRED EMBODIMENTS

Figure 1:
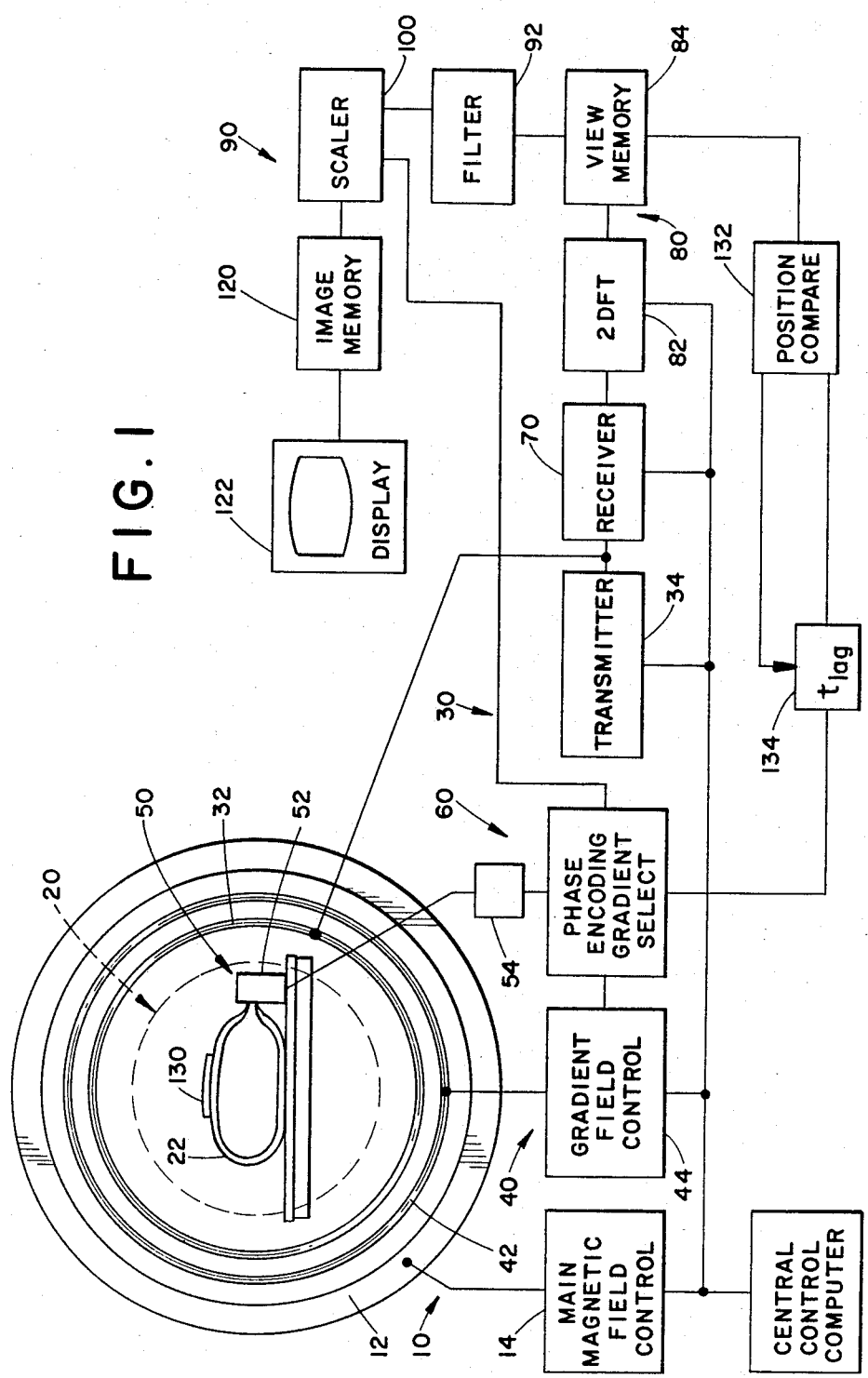
FIG. 1 is a diagrammatic illustration of a magnetic resonance imaging apparatus in accordance with the present invention.

With reference to FIG. 1, a main magnetic field generating means 10 generates a strong, generally uniform main magnetic field which extends generally longitudinally through an image region 20. A resonance excitation means 30 selectively excites magnetic dipoles of nuclei in the image region to precess about the main magnetic field. Each precessing magnetic dipole generates a component of a resonance signal.

A gradient field means 40 selectively causes gradients across the main magnetic field in the image region at selectable orientations. The gradient magnetic fields spatially encode the resonant signal components transmitted by the resonating dipoles within the image region. Specific to the preferred embodiment, the gradient magnetic fields encode spatial location along one axis in the frequency and encode spatial location along an orthogonal axis in the relative phase. The phase is encoded with one of a preselected set of phase encoding gradients. The set includes a central phase encoding gradient, preferably with zero value. The set extends through linearly incremented phase encoding gradients to a positive, maximum phase encoding gradient in one direction and to a negative phase encoding gradient in the other direction.

A monitoring means 50 monitors respiratory or other physical movement of a subject 22 in the image region 20. A phase encoding gradient selecting means 60 selects a phase encoding gradient from the preselected set in accordance with the monitored movement. Specifically, the selecting means selects a phase encoding gradient in accordance with the monitored physical movement such that during periods of least phsical movement, the selected phase encoding gradient is closest to the central value; during periods of greatest movement, the selected phase encoding gradient is distributed between the minimum and maximum values; and at intermediate ranges of movement, the selected phase encoding gradient is at proportionate intermediate values. Optionally, the selection criteria may be reversed such that the greatest movement is encoded at the central valve and the least movement is encoded at the minimum and maximum values. Any spatial frequency region may be selected to have the least motion.

A sampling means 70 discretely samples an integral number of data points of received resonance signals each with a unique phase encoding gradient. A transform means 80 transforms or maps each resonance signal from data space or the phase/frequency domain into a view in image space or the spatial domain. A calibration means 90 adjusts or filters each view to emphasize views with the least motion; scales to compensate for motion, and/or system non-linearities; and otherwise improve resolution or correct for distortion and artifacts. The views are summed in an image memory 120 to generate an image representation for display, storage, or further processing.

Although the preferred embodiment is described in conjunction with spin-echo two dimensional Fourier transform imaging, it is to be appreciated that the apparatus is applicable to hybrid imaging, echo planar imaging, projection reconstruction imaging, inversion recovery, saturation recovery, and other imaging techniques.

With continuing reference to FIG. 1, the main magnetic field means 10 includes a plurality of annular super-conducting or fluid cooled high power magnets 12 for generating the main magnetic field axially therethrough. A main magnetic field control circuit 14 controls and applies appropriate electrical power to the annular magnets such that a substantially uniform constant magnetic field is generated longitudinally therebetween. Commonly, the main magnetic field has a frequency in the one 5-100 MHz range.

The excitation means 30 includes a coil 32 which is connected with a radio frequency transmitter 34 for braodcasting radio frequency excitation pulses. The radio frequency pulses are of the appropriate timing and duration, as is known in the art, to cause precession of the magnetic dipoles about the applied magnetic field. In the illustrated embodiment, the coil 32 functions between excitation pulses as an antenna for receiving the radio frequency resonance signals. Optionally, a separate pick-up coil assembly may be provided.

The gradient field means 40 includes gradient field coils 42 which surround the image region for selectively applying gradient magnetic fields transversely across the main magnetic field. A gradient magnetic field control circuit 44 controls the application of gradient fields. As is known in the art, the gradient fields encode spatial position in selected slices of the subject with appropriate frequency and phase encoding. The phase encoding gradient is enclosed in accordance with the phase encoding gradient selected by the phase encoding gradient selection means 60.

The monitoring means 50 monitors the respiratory or other physical movement of the subject 22. In the preferred embodiment, the monitor means is a respiratory monitor 52 that includes a bellows arrangement to produce an output that varies in proportion to chest displacement. Preferably, a correlation adjustment means 54 allows the output signal of the monitor to be calibrated to the actual physical displacement of the subject undergoing examination. It should be recognized that other techniques are available which would allow the displacment to be monitored.

Figure 6:
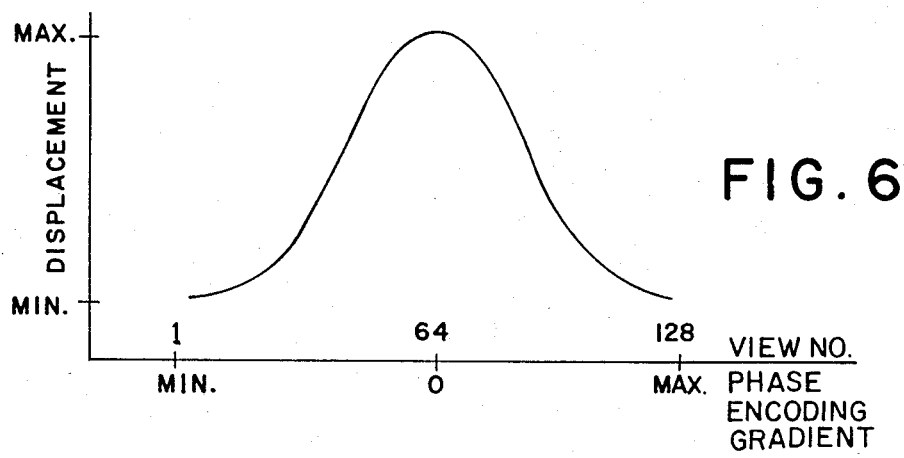

Ideally, a one-to-one mapping can be made from the monitored physical motion to the phase encoded gradients, such that a plot of phase encoded gradient value versus motion amplitude would yield a monotonically increasing function from the central value to the outer values (FIG. 2). Optimally, if the region of interest is the high spatial frequences, the mapping may show monotonically increasing values from the larger spatial frequencies to the center (FIG. 6). Because the same motion amplitude occurs periodically, the correspondingly encoded view may already have been collected.

To accomodate potentially redundant motion amplitudes, the one-to-one mapping is divided into sections, e.g. ten sections or bands (FIG. 2A). Each monitored amplitude retrieves the next available phase encoded gradient that corresponds to the band in which the monitored amplitude falls. This sectioning technique reduces memory requirements rendering it particularly advantageous in multiple slice and multiple averaging images.

With continuing reference to FIG. 1 and particular reference to FIG. 2, the phase selection means 60 selects the phase encoding gradient in accordance with the graphic display of FIG. 2. That is, the physical displacement of the chest from the means correlation 54 indexes the corresponding displacement amplitude along the ordinate axis of FIG. 2. The corresponding phase encoding gradient along the abscissa axis which is related by the illustrated curve 62 is selected to provide the phase encoding gradient of the gradient encoding for the next view. The phase selection means 60 includes a memory for remembering which phase encoded views have been taken so that the same phase gradient is not applied twice in one image. For example, the first time an exemplary physical displacement 66 is addressed, a first phase encoding gradient 66a of the two possible views or phase encodient gradients is selected. The second time the same physical displacement 66 is addressed, the other corresponding phase encoding gradient or view 66b is selected. If the same displacement is addressed a third time, the most closely adjacent phase encodient gradient or view along the curve which has not yet been used is selected. Constraints can be applied which allow views associated with large amplitudes of motion to be selectively re-acquired. This allows a further improvement in resolution with a minimal, and if desired, fixed increase in time.

A further improvement in resolution can be obtained by interpolating each view of the data. The interpolation is based on the actual point to point movement, such as of the patient's chest. A spatial and or temporal model of the periodic motion may be developed. The interpolation is then selected in accordance with the motion as predicted by the model.

The sampling means 70 includes a receiver which receives the analog resonance signal that includes a large multiplicity of superimposed resonance signal components. The frequency and relative phase of each component is indicative of the encoded spatial position of the corresponding generating dipole. The receiver discretely samples each received resonance signal to generate one view of digital resonance signal data. Each view of data is two dimensionally transformed or mapped by a fast Fourier transform or other appropriate transform (such as a generalized transform which may avoid or minimize errors due to interpolation) or reconstructing means 82 from the frequency and phase domain into a two dimensional spatial domain view which is stored in an intermediate memory means 84.

The calibration means 90 includes a filter means 92 for emphasizing the views taken with the phase encoding gradients which correspond to the least physical displacement, in the preferred embodiment the phase encoding gradients closest to the central phase encoding gradient. In the preferred embodiment, the filter means 92 includes a low pass filter which attenuates or eliminates views having a phase e.g. equivalent to spatial frequencies above or below preselected frequencies 94a and 94b of FIG. 2. Optionally, a filter function 96, such as illustrated in FIG. 3, may be utilized to emphasize views near the central phase encoding value and progressively de-emphasizes views at higher and lower phase encoding gradients.

A scaling means 100 shifts the pixels of each view in accordance with the degree of physical movement, e.g. respiratory displacement. In the preferred embodiment, the pixels are scaled or shifted in accordance with the amplitude of the motion at a given phase encoding gradient at which the view was taken.

Figure 4:
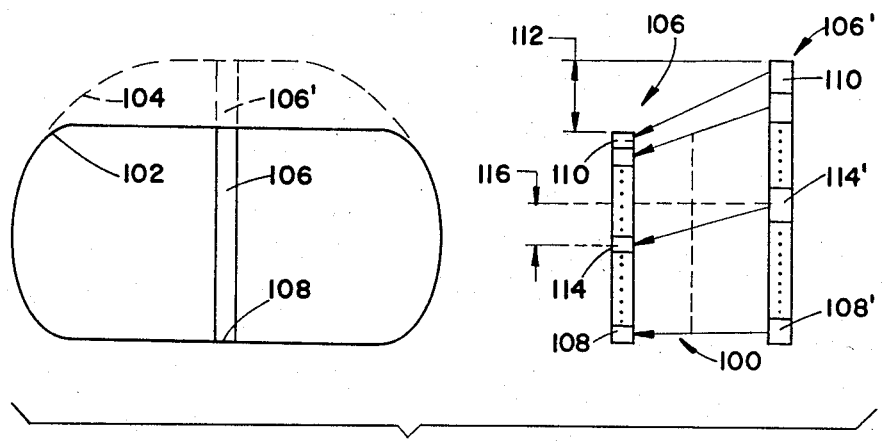
FIG. 4 illustrates a scaling correction for respiratory motion.

With reference to FIG. 4, the motion varies from a first extreme or rest position 102 to a second extreme or maximum expansion position 104. A linear column of pixels 106 vertically through the center of the patient cylically stretches from the rest position 106 to the expansion position 106'. The patient's back 108 remains stationary while a front or top portion 110 moves the farthest distance 112. Portions of the patient in between, such as central position 114, move a predictable intermediate distance 116. To compensate for this motion, data from a region 108' of the patients back becomes data 108 representing the same location; data corresponding to a central portion 114' of the patient in the expanded position is shifted or contracted along a vertical axis to represent the central position at a preselected degree of chest expansion 114; and, front portion data 110' is positionally shifted to become data representing incremental element 110. In this manner, data taken in the expanded position 106' is scaled or shifted in accordance with the monitored movement such that the resultant data represents a patient in the rest position 106.

Figure 5:
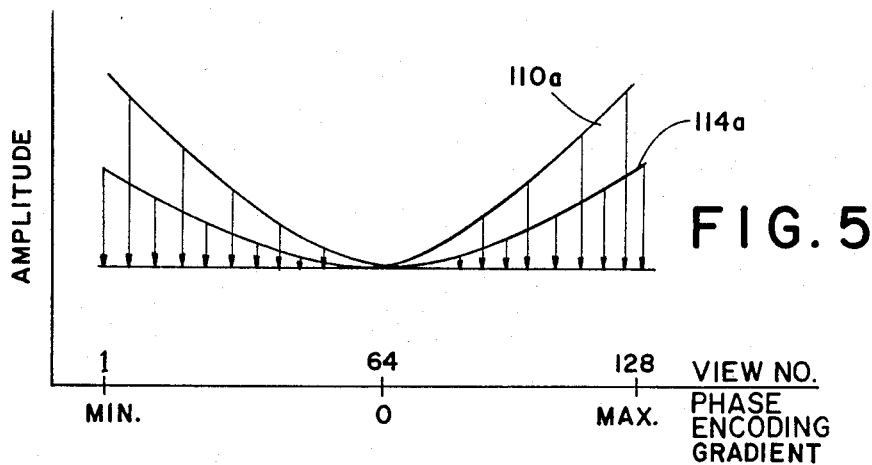
FIG. 5 illustrates a relationship between scaling correction and phase encoding gradients; and, FIG. 6 is a graphic illustration of an alternate embodiment of a centrally ordered phase encoding scheme in accordance with the present invention.

FIG. 5 illustrates the relationship between the phase encoding gradient and the effect relative shifting of typical pixels. Curve 110a illustrates the effective amplitude or vertical displacement correction for the pixel corresponding to the patient top portion 110. Curve 114a illustrates the effective amplitude or vertical displacement correction for the central pixel 114. The data in each pixel is analogously shifted downward to the rest or other selected position in accordance with the phase encoding gradient. For example, a phase encoding gradient which corresponds to 2 cm. of movement of the upper chest may cause pixels along the top of the subject to be shifted downward by 2 cm., the pixels along the center pixel 114 to be shifted downward 1 cm., pixels at the bottom 108 to be unmoved, and proportionately for pixels in between.

Each of the filtered and scaled views is transformed and stored into the image memory 120. A video monitor 122 provides a man-readable display of the image. Optionally the image may be recorded on a tape or disk for later use or processing.

With reference to FIG. 6, the phase selection means 60 may centrally order the phase encoding gradient of views with the greatest physical displacement. The minimal physical displacement is phase encoded with the maximum and minimum phase encoding gradients. With this alternate ordering, the filter means 92 includes a low pass filter or a filter which is the complement of FIG. 3 for attenuating the central phase encoded gradient data relative to the phase encoded data collected at the phase encoding gradient extremes. Other phase encoding ordering may also be implemented as is appropriate to the data to be emphasized and de-emphasized.

Alternately, the motion sensing means 50 may sense the respiratory or other motion electronically. A control strip or member 130 of readily recognizable characteristics is positioned on the moving surface of the patient to be imaged therewith. A position comparing means 132 compares the relative position of the control strip 130 in each reconstructed view as it is received in the temporary memory means 82. The position of the central strip is, of course, indicative of the degree of respiratory expansion. Optionally, the comparing means may monitor a selected portion of the subject, such as the interface between the subject and the ambient atmosphere, heart wall portions or values, and the like. A time delay or movement compensating means 134 compensates for motion between the detection of the motion and the acquisition of the data. That is, the compensating means 134 multiplies the duration between the detection of the motion and the acquisition of the data by the speed with which the control member 130 is moving and adds this adjustment to the position determined by the position determining means 132. The phase encoding gradient selection means 60 selects the phase encoding gradient in accordance with the monitored physical position.

The invention has been described with reference to the preferred embodiment. Obviously, alterations and modifications will occur to others upon reading and understanding the preceding specification. It is intended that the invention be construed as including all such alterations and modifications in so far as they come within the scope of the appended claims or the equivalents thereof.

Having thus described the preferred embodiments, the invention is now claimed to be:

1. A method of magnetic resonance imaging comprising:
   (a) monitoring physical movement of at least a portion of a subject in an image region;
   (b) exciting magnetic resonance of magnetic dipoles of at least a portion of the subject disposed in the image region;
   (c) selecting a phase encoding gradient from a range of phase encoding gradients, which phase encoding gradient range includes a maximum phase encoding gradient, a minimum phase encoding gradient, and a multiplicity of phase encoding gradients therebetween including a central value, the phase encoding gradient is selected in accordance with the physical movement such that during first periods of physical movement the selected phase encoding gradient is closest to the central value and during second preselected periods of physical movement, the selected phase encoding gradient is distributed between the minimum and maximum phase encoding values;
   (d) phase encoding magnetic field gradients in the image region with the selected phase encoding gradients;
   (e) receiving resonance signals from the resonating dipoles in the image region; and,
   (f) reconstructing an image representation of the portion of the subject in the image region from the resonance signals.

2. The method as set forth in claim 1 wherein the first preselected period is during respiratory relaxation and the second preselected period is during maximum respiratory inhalation.

3. The method as set forth in claim 1 wherein in the phase encoding gradient selecting steps, the central phase encoding gradient is selected during periods of least physical movement, the minimum and maximum phase encoding gradients are selected during periods of greatest physical movement, and intermediate values are selected during proportionate intermediate degrees of physical movement between the least and most physical movement.

4. The method as set forth in claim 3 further including the step of reducing the effect of received resonance signals which are phase encoded with values adjacent the minimum and maximum phase encoding gradients in the reconstructed image representation.

5. The method as set forth in claim 1 wherein the reconstructing step includes reordering the received resonance signals into view representations and transforming the view representations into the image representation.

6. The method as set forth in claim 5 further including the step of scaling the physical position within each view to compensate for the physical motion such that the moving portions are shifted to a preselected position.

7. The method as set forth in claim 5 wherein the monitoring step is conducted electronically by measuring motion in each reconstructed view, such that the phase encoding gradient is selected from the measured motion in a preceding view.

8. The method as set forth in claim 5 wherein the selecting step includes selecting phase encoding gradients closest to the central value corresponding to periods of least physical movement.

9. The method as set forth in claim 8 further including the step of weighting views encoded adjacent the central phase encoding gradient more heavily and views collected adjacent the minimum and maximum phase encoding gradients less heavily when transforming the views to form an image representation.

10. A method of magnetic resonance imaging comprising:
    (a) monitoring physical movement of at least a portion of a subject in an image region;
    (b) exciting magnetic resonance of magnetic dipoles of at least a portion of the subject disposed in the image region;
    (c) receiving resonance signals from the resonating dipoles in the image region;
    (d) reordering the received resonance signals into an electronic data view for transformation into an image representation;
    (e) scaling the electronic data view in accordance with the monitored physical movement to shift each of the moving subject portions represented by the electronic view to represent a preselected subject position;
    (f) repeating steps (a) through (e) as the subject moves such that the scaling of step (e) changes with the subject movement;
    (g) combining a plurality of the electronic data views scaled into an image, whereby a first order correction to remove blurring from motion caused position indefiniteness is made.

11. A method of magnetic resonance imaging comprising:
    (a) monitoring physical movement of at least a portion of a subject in an image region;
    (b) exciting magnetic resonance in at least a portion of the subject disposed in the image region;
    (c) selecting a phase encoding gradient from a range of gradients in accordance with the monitored physical movement;
    (d) phase encoding magnetic field gradients in the image region with the selected phase encoding gradient;
    (e) receiving phase encoded resonance signals from the image region;
    (f) converting the received resonance signals into view representations for transformation into an image representation; and,
    (g) scaling each view representation in accordance with the monitored physical movement to shift the moving subject portions of the view representations to a preselected subject position, whereby a first order correction to remove blurring from motion caused position indefiniteness and a second order correction to remove motion relates ghosting are made.

12. An apparatus for magnetic resonance imaging, the apparatus comprising:
(a) a main magnetic field means for creating a main magnetic field through an image region;
(b) a magnetic resonance excitation means for exciting magnetic resonance of magnetic dipoles in the image region;
(c) a magnetic field gradient means for causing magnetic field gradients across the main magnetic field at least in the image region for at least phase encoding the magnetic resonance signals;
(d) a phase encoding gradient selection means for selecting a phase encoding gradient in accordance with physical movement of a portion of a subject in the image region, the phase encoding gradient selecting means selecting a phase encoding gradient near a central value when the physical movement is adjacent one extreme movement and selecting a phase encoding gradient adjacent minimum and maximum phase encoding values when the monitored physical movement is adjacent a second extreme of movement, the phase encoding gradient selecting means being operatively connected with the magnetic field gradient means;
(e) a transform means for transforming resonance signals collected with each phase encoding gradient into an intermediate view.

13. The apparatus as set forth in claim 12 further including a monitoring means for monitoring physical movement of at least a portion of a subject within the imaging region, the monitoring means being operatively connected with the phase encoding gradient selection means.

14. The apparatus as set forth in claim 13 wherein the monitoring means includes means for monitoring a respiratory cycle of the subject and determining a degree of chest expansion between a minimum expansion extreme and a maximum chest expansion extreme.

15. The apparatus as set forth in claim 14 wherein the phase encoding gradient selection means selects the central phase ecoding gradient value at the minimum expansion extreme and selects the minimum and maximum phase encoding gradients at the adjacent the maximum expansion extreme.

16. The apparatus as set forth in claim 15 further including a filter means for weighting each intermediate view in accordance with the selected phase encoding gradient such that views encoded adjacent the central phase encoding gradient are weighted more heavily than views encoded adjacent the minimum and maximum phase encoding gradients and image memory means for summing a plurality of the weighted views to form an image representation.

17. The apparatus as set forth in claim 12 further including a scaling means for scaling data within each intermediate view for electronically shifting data from the moving subject portion into a preselected motion state, the scaling means being operatively connected with the transforming means and with the phase encoding gradient selection means.

18. The apparatus as set forth in claim 17 further including a filter means for weighting each view in accordance with the selected phase encoding gradient and image memory means for transforming a plurality of the weighted and scaled views to form an image representation.

19. An apparatus for magnetic resonance imaging, the apparatus comprising:
(a) a main magnetic field means for creating a main magnetic field through an image region;
(b) a magnetic resonance excitation means for exciting magnetic resonance of magnetic dipoles in the image region;
(c) a magnetic field gradient means for causing magnetic field gradients across the main magnetic field at least in the image region for at least phase encoding the magnetic resonance signals;
(d) a transform means for transforming resonance signals collected with each phase encoding gradient into an intermediate view;
(e) a scaling means for selectively expanding and correcting the intermediate views along at least one axis for electronically shifting data from the moving subject portion into data representing a preselected motion state, the scaling means being operatively connected with the transforming means; and,
(f) an image memory means operatively connected with the scaling means into which the scaled intermediate views are summed.

20. An apparatus for magnetic resonance imaging, the apparatus comprising:
(a) a main magnetic field means for creating a main magnetic field through an image region;
(b) a magnetic resonance excitation means for exciting magnetic resonance in the image region;
(c) a magnetic field gradient means for causing magnetic field gradients across the main magnetic field at least in the image region for at least phase encoding the magnetic resonance signals;
(d) a phase encoding gradient selection means for selecting the phase encoding gradient in accordance with monitored physical movement of a portion of a subject in the image region, the phase encoding gradient selecting means being operatively connected with the magnetic field gradient means;
(e) a transform means for transforming resonance signals collected with each phase encoding gradient into an intermediate view; and,
(f) a scaling means for scaling data within each intermediate view for electronically shifting data from the moving subject portion into a preselected motion state, the scaling means being operatively connected with the transforming means.

21. The apparatus as set forth in claim 20 further including a filter means for weighting each intermediate view in accordance with the selected phase encoding gradient , the filter means being operatively connected with the scaling means to receive scaled, intermediate views therefrom.

22. An apparatus for magnetic resonance imaging, the apparatus comprising:
(a) a main magnetic field means for creating a main magnetic field through an image region;
(b) a magnetic resonance excitation means for exciting magnetic resonance of magnetic dipoles in the image region;
(c) a magnetic field gradient means for causing magnetic field gradients across the main magnetic field at least in the image region for at least phase encoding the magnetic resonance signals;

(d) a phase encoding gradient selection means for selecting a phase encoding gradient in accordance with physical movement of a portion of a subject in the image region, the phase encoding gradient selection means being operatively connected with the magnetic field gradient means;

(e) a transforming means for transforming resonance signals encoded with each selected phase encoding gradient into a corresponding view;

(f) a filter means for weighting each view in accordance with the selected phase encoding gradient such that views with preselected phase encoding gradients are weighted more heavily than views encoded with other phase encoding gradients; and, (g) an image memory means into which the weighted views are transformed and stored to form an image representation.

23. The apparatus as set forth in claim 22 further including a monitoring means for monitoring the physical movement of the subject within the imaging region, the monitoring means being operatively connected with the phase encoding gradient selecting means.

24. The apparatus as set forth in claim 23 wherein the phase encoding gradient selection means selects phase encoding gradients centrally within a range for movement adjacent a first position and wherein the filter means weights centrally encoded views most heavily such that the image representation emphasizes movement adjacent the first position.

25. The apparatus as set forth in claim 22 further including a scaling means for spatially adjusting each view in accordance with the selected phase encoding gradient to compensate for the physical movement.

* * * * *